(12) United States Patent
Godo et al.

(10) Patent No.: US 12,137,869 B2
(45) Date of Patent: Nov. 12, 2024

(54) IMAGE PROCESSING APPARATUS, ENDOSCOPE SYSTEM, AND IMAGE PROCESSING METHOD

(71) Applicant: OLYMPUS CORPORATION, Tokyo (JP)

(72) Inventors: Hirokazu Godo, Hachioji (JP); Yamato Kanda, Hino (JP); Yukihiro Sugimoto, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 702 days.

(21) Appl. No.: 17/200,105

(22) Filed: Mar. 12, 2021

(65) Prior Publication Data
US 2021/0196100 A1    Jul. 1, 2021

Related U.S. Application Data

(63) Continuation of application No. PCT/JP2018/034934, filed on Sep. 20, 2018.

(51) Int. Cl.
*A61B 1/00* (2006.01)
*G06T 7/11* (2017.01)

(52) U.S. Cl.
CPC .. *A61B 1/000094* (2022.02); *A61B 1/000095* (2022.02); *A61B 1/00016* (2013.01); *A61B 1/00045* (2013.01); *G06T 7/11* (2017.01)

(58) Field of Classification Search
CPC .............. A61B 1/041; A61B 1/000094; A61B 1/00009; A61B 1/00045; A61B 1/000095; A61B 1/0005; A61B 1/05; A61B 1/00016; A61B 1/045; G06T 7/0012; G06T 2207/10068; G06T 2207/30004; G06T 7/11; G06T 1/00; H04N 7/18; H04N 23/00
See application file for complete search history.

(56) References Cited

U.S. PATENT DOCUMENTS 9,186,051 B2 * 11/2015 Hirota .................... G06T 7/0016
9,959,481 B2 *  5/2018 Kitamura ................ G06F 18/22
(Continued)

FOREIGN PATENT DOCUMENTS

EP    1924082 A2    5/2008
JP    H10165363 A  *  6/1998
(Continued)

OTHER PUBLICATIONS

International Search Report dated Dec. 4, 2018 issued in PCT/JP2018/034934.

*Primary Examiner* — Ian L Lemieux
*Assistant Examiner* — Woo C Rhim
(74) *Attorney, Agent, or Firm* — Scully, Scott, Murphy & Presser, P.C.

(57) ABSTRACT

An image processing apparatus includes a processor. The processor is configured to output second and third images corresponding to a continuous first image respectively to first and second routes, analyze the second image and output an analysis result, and generate a fourth image based on the third image and the analysis result and continuously output the fourth image. When acquiring the third image, the processor completes the generation of the fourth image before acquiring an analysis result by the second image generated based on a same first image as the first image, which is a generation source of the third image.

18 Claims, 14 Drawing Sheets

(56) References Cited

U.S. PATENT DOCUMENTS

| | | | |
|---|---|---|---|
| 2003/0063398 A1* | 4/2003 | Abe | G02B 23/2438 |
| | | | 359/823 |
| 2006/0149133 A1* | 7/2006 | Sugimoto | A61B 1/043 |
| | | | 600/178 |
| 2008/0144960 A1 | 6/2008 | Watarai | |
| 2018/0110399 A1* | 4/2018 | Mizukami | A61B 1/07 |
| 2019/0328218 A1* | 10/2019 | Sato | A61B 1/07 |
| 2020/0135330 A1* | 4/2020 | Sugie | G06V 10/147 |

FOREIGN PATENT DOCUMENTS

| | | | | |
|---|---|---|---|---|
| JP | 2003102675 A * | 4/2003 | | A61B 1/00009 |
| JP | 2008124976 A * | 5/2008 | | G06T 5/002 |
| JP | 2013-17752 A | 1/2013 | | |
| JP | 2013017752 A * | 1/2013 | | |
| JP | 5317886 B2 * | 10/2013 | | |
| JP | 2014128423 A * | 7/2014 | | |
| JP | 2017000839 A * | 1/2017 | | A61B 1/00009 |
| WO | WO-2018150627 A1 * | 8/2018 | | A61B 1/045 |

* cited by examiner

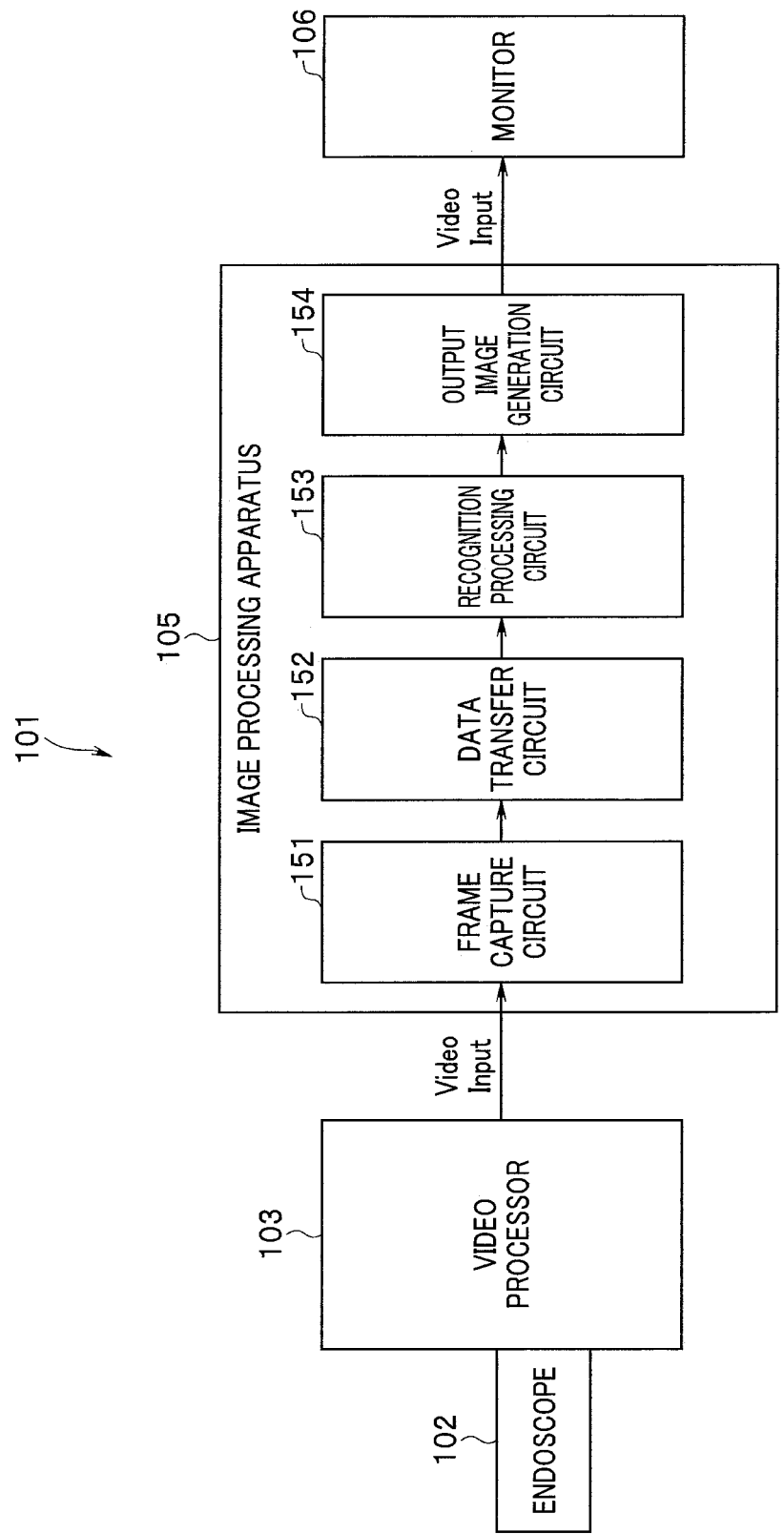

IMAGE PROCESSING APPARATUS, ENDOSCOPE SYSTEM, AND IMAGE PROCESSING METHOD

CROSS REFERENCE TO RELATED APPLICATION

This application is a continuation application of PCT/JP2018/034934 filed on Sep. 20, 2018, the entire contents of which are incorporated herein by this reference.

BACKGROUND OF THE INVENTION

1. Field of the Invention

The present invention relates to an image processing apparatus, an endoscope system, and an image processing method and, more particularly, to an image processing apparatus, an endoscope system, and an image processing method for performing processing by a computer-aided diagnosis (CAD).

2. Description of the Related Art

An endoscope system including an endoscope that picks up an image of an object on an inside of a subject and a video processor that generates an observation image of the object, the image of which is picked up by the endoscope, has been widely used in a medical field, an industrial field, and the like.

On the other hand, in recent years, there has been known image processing (recognition processing) for performing processing by a so-called computer-aided diagnosis (CAD) for performing, with an information processing technique by a computer or the like, quantization and an analysis of information concerning an image obtained by an endoscope or the like and actively using a result of the quantization and the analysis for an image diagnosis.

The computer-aided diagnosis (CAD) is, in general, a system that supports doctors. In other words, the computer-aided diagnosis (CAD) is an aiding system in which the computer itself does not determine a disease name and the like but only provides determination material for a doctor who performs final decision making.

For example, in a case in which it is difficult to perform decision making such as malignity and benignancy discrimination of a quantitative result focus analyzed using a computer, the computer-aided diagnosis (CAD) aids decision making of a doctor by presenting information (quantitative numerical values and the like analyzed by the computer) serving as material.

It is known that recognition processing used for the computer-aided diagnosis (CAD) requires enormous computation processing.

FIG. 14 is a diagram showing an example of an endoscope system that makes use of the computer-aided diagnosis (CAD) function explained above. An endoscope system 101 shown in FIG. 14 is a system including an image processing apparatus 105 including a recognition processing circuit 153 that exerts the computer-aided diagnosis (CAD) function.

As shown in FIG. 14, in the endoscope system 101 including the image processing apparatus 105 including the recognition processing circuit 153, after a publicly-known video processor 103 applies predetermined image processing to an endoscopic image picked up in an endoscope 102, the image processing apparatus 105 applies predetermined recognition processing to the endoscopic image.

More specifically, in the image processing apparatus 105, a frame capture circuit 151 and a data transfer circuit 152 continuously capture inputted images and transmit the images to the recognition processing circuit 153. Thereafter, the recognition processing circuit 153 carries out recognition processing based on the computer-aided diagnosis (CAD) function explained above. An image signal subjected to the recognition processing in the recognition processing circuit 153 is outputted to a monitor 106 through a predetermined output image generation circuit 154.

In the recognition processing carried out in the recognition processing circuit 153, in general, a so-called GP-GPU (general-purpose computing on graphics processing units) is used.

The GP-GPU is a general-purpose computation processing technique by a GPU (graphics processing units). In recent years, processing speed of the GP-GPU has been further increased.

SUMMARY OF THE INVENTION

An image processing apparatus according to an aspect of the present invention includes a processor. The processor is configured to: output a second image information signal corresponding to a continuous first image information signal to at least a first route and output a third image information signal, which is an image information signal corresponding to the first image information signal, to a second route; apply a predetermined analysis to the second image information signal and output an analysis result; acquire the third image information signal and the analysis result and generate a fourth image information signal based on the third image information signal and the analysis result and continuously output the fourth image information signal; and, when acquiring the third image information signal in the generation and the continuous output of the fourth image information signal, complete the generation of the fourth image information signal before acquiring the analysis result by the second image information signal generated based on a same first image information signal as the first image information signal, which is a generation source of the third image information signal.

An endoscope system according to an aspect of the present invention includes: an endoscope that observes a subject and outputs an image pickup signal; and an image processing apparatus including a processor. The processor is configured to output a second image information signal corresponding to a continuous first image information signal based on the image pickup signal to at least a first route and output a third image information signal, which is an image information signal corresponding to the first image information signal, to a second route, apply a predetermined analysis to the second image information signal and output an analysis result, acquire the third image information signal and the analysis result and generate a fourth image information signal based on the third image information signal and the analysis result and continuously output the fourth image information signal, and, when acquiring the third image information signal in the generation and the continuous output of the fourth image information signal, complete the generation of the fourth image information signal before acquiring the analysis result by the second image information signal generated based on a same first image information signal as the first image information signal, which is a generation source of the third image information signal.

An image processing method according to an aspect of the present invention includes: outputting a second image information signal corresponding to a continuous first image information signal to at least a first route and outputting a third image information signal, which is an image information signal corresponding to the first image information signal, to a second route; applying a predetermined analysis to the second image information signal and outputting an analysis result; acquiring the third image information signal and the analysis result and generating a fourth image information signal based on the third image information signal and the analysis result and continuously outputting the fourth image information signal; and, when acquiring the third image information signal in the generation and the continuous output of the fourth image information signal, completing the generation of the fourth image information signal before acquiring the analysis result by the second image information signal generated based on a same first image information signal as the first image information signal, which is a generation source of the third image information signal.

BRIEF DESCRIPTION OF THE DRAWINGS

FIG. 14 is a block diagram showing a configuration example of a conventional image processing apparatus capable of executing recognition processing such as a computer-aided diagnosis (CAD).

DETAILED DESCRIPTION OF THE PREFERRED EMBODIMENTS

Embodiments of the present invention are explained below with reference to the drawings.

First Embodiment

Figure 1:
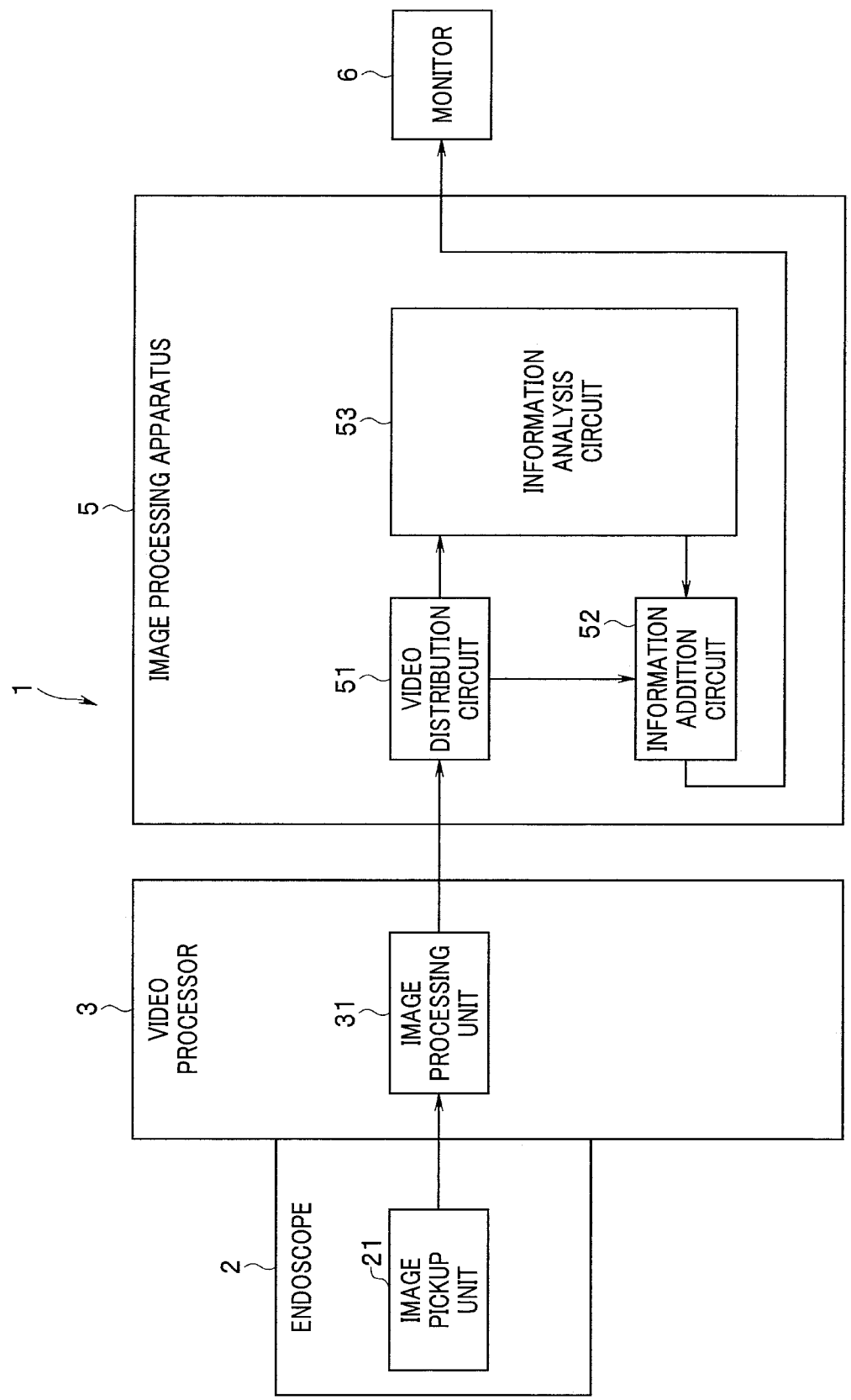
FIG. 1 is a block diagram showing a configuration of an endoscope system including an image processing apparatus according to a first embodiment of the present invention.
Figure 2:
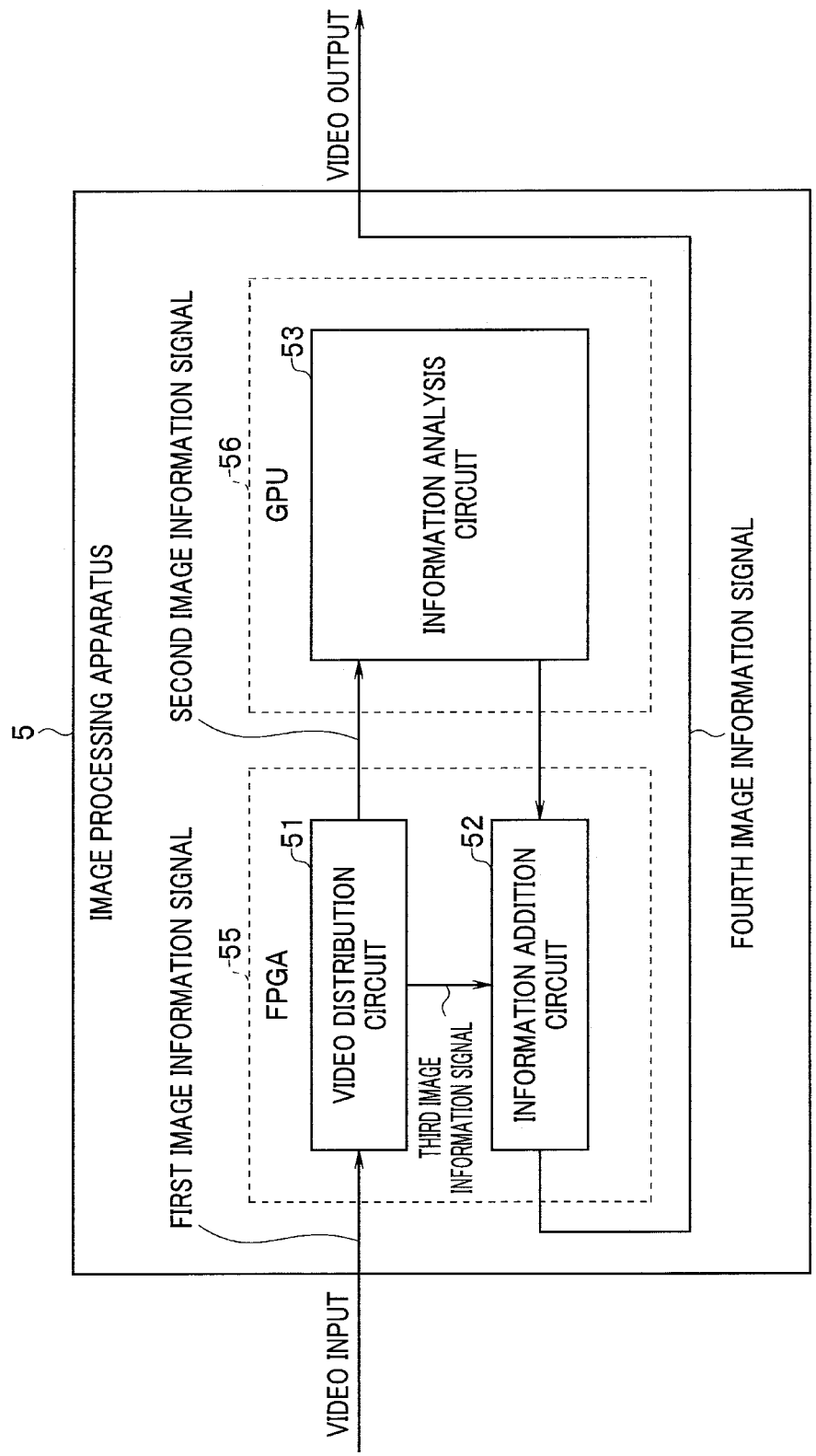
FIG. 2 is a block diagram showing a configuration of the image processing apparatus in the first embodiment.

FIG. 1 is a block diagram showing a configuration of an endoscope system including an image processing apparatus according to a first embodiment of the present invention. FIG. 2 is a block diagram showing a configuration of the image processing apparatus in the first embodiment.

As shown in FIG. 1, an endoscope system 1 including the image processing apparatus according to the first embodiment includes an endoscope 2 that observes a subject and outputs a predetermined image pickup signal, a video processor 3 that is connected to the endoscope 2, receives the image pickup signal, applies predetermined image processing to the image pickup signal, and outputs the image pickup signal, a not-shown light source apparatus that supplies illumination light for illuminating the subject, an image processing apparatus 5 that receives the image pickup signal outputted from the video processor 3, applies predetermined recognition processing to the image pickup signal, and outputs the image pickup signal, and a monitor 6 that displays an observation image corresponding to the image pickup signal outputted from the image processing apparatus 5.

As shown in FIG. 1, the endoscope 2 includes a publicly-known insertion section inserted into a body cavity of the subject. An image pickup unit 21 configured by a publicly-known image pickup device or the like is disposed at a distal end of the insertion section. An image pickup signal relating to the subject is outputted from the image pickup unit 21.

In the video processor 3, an image processing unit 31 that is connected to the endoscope 2 and receives the image pickup signal and applies predetermined image processing to the image pickup signal is disposed. The image pickup signal applied with the predetermined image processing is outputted from the image processing unit 31. Note that when an output of the image processing unit 31 is directly connected to a display apparatus such as the monitor 6, an endoscopic image relating to the image pickup signal outputted from the image processing unit 31 can be directly displayed on the monitor 6.

<Configuration of the Image Processing Apparatus 5>

The image processing apparatus 5 includes a processor. The processor is configured by an integrated circuit including circuit units corresponding to respective units in the image processing apparatus 5. Examples of the integrated circuit are, as explained below, a GP-GPU (general-purpose computing on graphics processing units), an FPGA (field-programmable gate array), and the like. However, the processor is not limited to this configuration. The processor may be configured by electronic circuits corresponding to the respective units in the image processing apparatus 5. When necessary processing speed can be obtained, the processor may be configured to cause a CPU or the like to execute software.

As shown in FIG. 1 and FIG. 2, the image processing apparatus 5 includes a video distribution circuit 51 that receives a first image information signal outputted from the video processor 3, distributes the first image information signal to a second image information signal and a third image information signal, and outputs the second image information signal and the third image information signal, an information analysis circuit 53 that receives the second image information signal outputted from the video distribution circuit 51, applies a predetermined analysis to the second image information signal, and outputs an analysis result, and an information addition circuit 52 that generates a fourth image information signal based on the third image information signal outputted from the video distribution circuit 51 and the analysis result outputted from the information analysis circuit 53 and continuously outputs the fourth image information signal.

As shown in FIG. 2, in the present embodiment, the video distribution circuit 51 and the information addition circuit 52 are configured as circuits formed in a so-called FPGA (field-programmable gate array) 55 disposed in the image processing apparatus 5.

In the present embodiment, the information analysis circuit 53 is a circuit configured by a GP-GPU (general-purpose computing on graphics processing units) 56, which is a general-purpose computation processing technique by a GPU (graphics processing units).

<Configuration of the Video Distribution Circuit 51>

A configuration of the video distribution circuit 51 is explained in detail.

Figure 3:
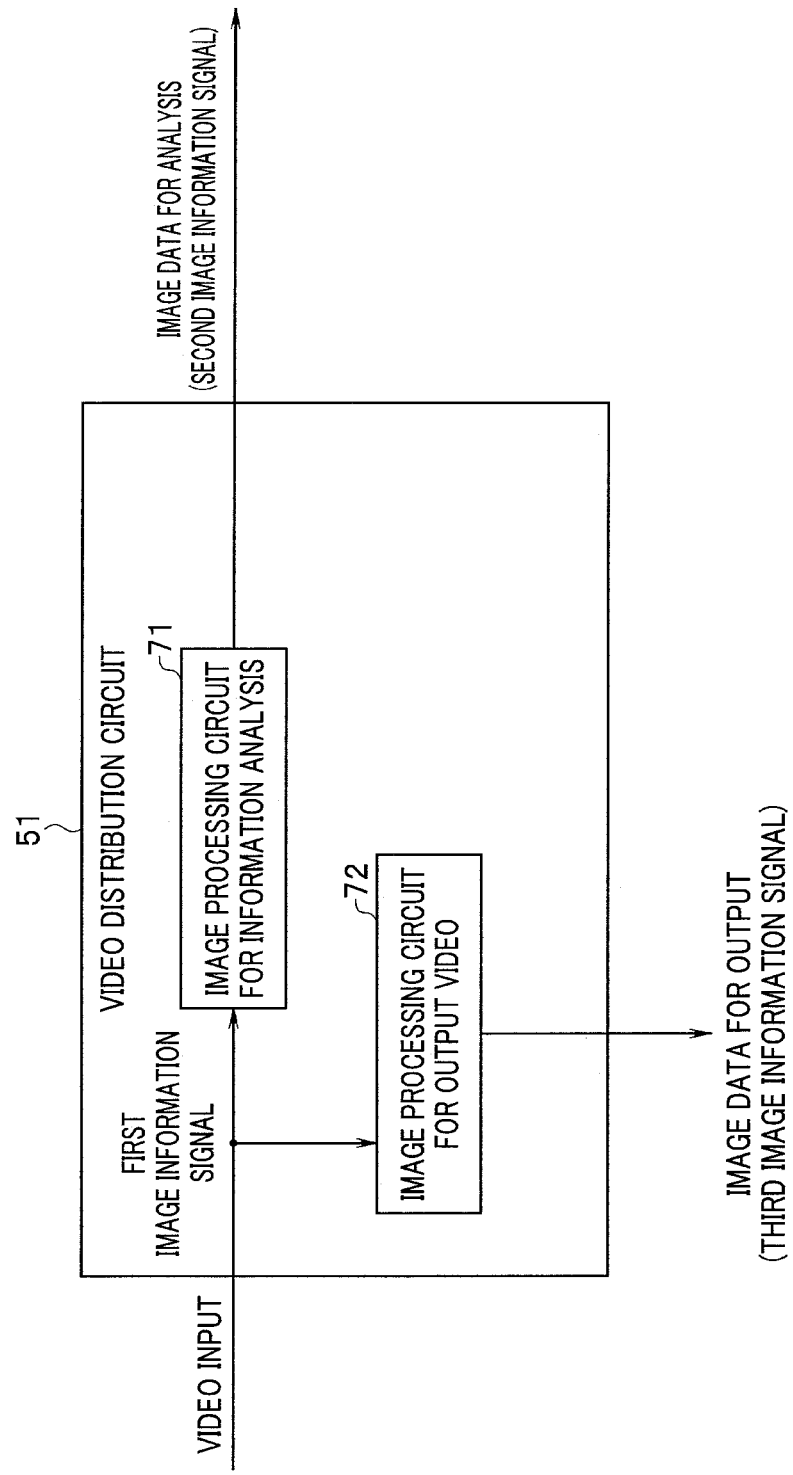
FIG. 3 is a block diagram showing a configuration of a video distribution circuit in the image processing apparatus in the first embodiment.

FIG. 3 is a block diagram showing the configuration of video distribution circuit 51 in the image processing apparatus 5 in the present embodiment.

As shown in FIG. 2 and FIG. 3, the video distribution circuit 51 receives the first image information signal continuously outputted from the video processor 3, which is an external apparatus, outputs the second image information signal corresponding to the inputted first image information signal to at least a first route, and outputs the third image information signal, which is an image information signal corresponding to the first image information signal and is different from the second image information signal, to a second route.

<Image Processing Circuit for Information Analysis 71>

In other words, the video distribution circuit 51 includes an image processing circuit for information analysis 71 that generates the second image information signal (image data for analysis) based on the first image information signal and outputs the second image information signal. The image processing circuit for information analysis 71 generates image data for analysis for a predetermined analysis in the information analysis circuit 53 based on the inputted first image information signal and outputs the image data for analysis as the second image information signal.

In the present embodiment, first, the image processing circuit for information analysis 71 segments a predetermined region (a region to which the information analysis circuit 53 explained below applies recognition processing) in the inputted first image information signal, generates the image data for analysis relating to the segmented region, and outputs the image data for analysis to the first route as the second image information signal.

Figure 7:
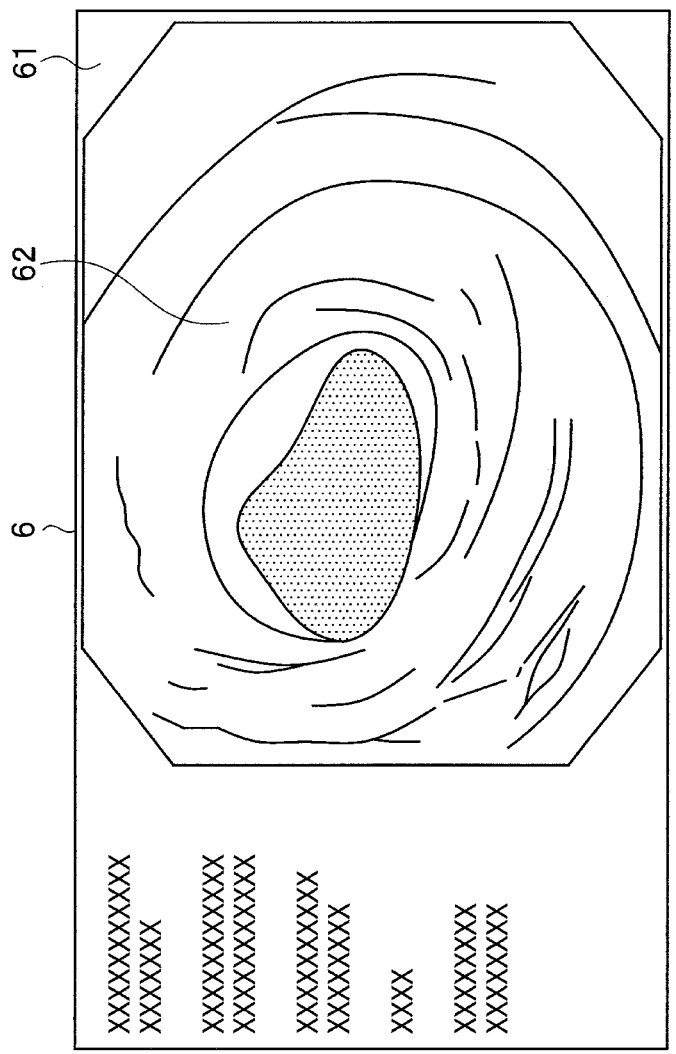
FIG. 7 is a diagram showing an example of a first image information signal inputted to the image processing apparatus in the first embodiment.

More specifically, it is assumed that the first image information signal (for example, an entire image signal including an endoscopic image 62 shown in FIG. 7) outputted from the video processor 3 is inputted to the image processing apparatus 5 now. Note that FIG. 7 is a diagram showing an example of the first image information signal inputted to the image processing apparatus in the first embodiment and shows a state in which an image of the entire first image information signal including the endoscopic image 62 is displayed on a display screen 61 of the monitor 6.

At this time, the first image information signal including the endoscopic image 62 outputted from the video processor 3 is inputted to the image processing circuit for information analysis 71 in the image processing apparatus 5.

The image processing circuit for information analysis 71 in the present embodiment segments the endoscopic image 62, which is a predetermined region, from the first image information signal. In the present embodiment, the predetermined region to be segmented is the endoscopic image 62 having a so-called octagonal mask shape. Note that an image data amount relating to the endoscopic image 62 is smaller compared with a data amount of the entire first image information signal.

Thereafter, the image processing circuit for information analysis 71 generates the image data for analysis relating to the segmented endoscopic image 62 and outputs the image data for analysis toward the information analysis circuit 53 at a post-stage (through the first route) as the second image information signal.

The image processing circuit for information analysis 71 generates the image data for analysis obtained by leveling predetermined physical characteristics (for example, a color setting value, a γ value, brightness, and a highlighting degree of a contour) relating to the inputted first image information signal and outputs the image data for analysis to the first route as the second image information signal.

In other words, it is likely that, in the inputted first image information signal, various settings are made according preferences of a surgeon for the physical characteristics (the color setting value, the γ value, the brightness, the highlighting degree of the contour, and the like) in, for example, the video processor 3 or the like at a pre-stage. The image processing circuit for information analysis 71 contributes to improving accuracy of recognition processing at a post-stage, that is, in the information analysis circuit 53 by once leveling an image signal to which these various settings are already applied.

<Image Processing Circuit for Output Video 72>

On the other hand, the video distribution circuit 51 includes an image processing circuit for output video 72 that generates the third image information signal based on the first image information signal and outputs the third image information signal. The image processing circuit for output video 72 generates the third image information signal (image data for output) obtained by applying predetermined image processing to the inputted first image information signal (an image pickup signal relating to an endoscopic image outputted from the video processor 3) and outputs the third image information signal to the second route as a signal, a delay of which is minimized.

Note that the image processing circuit for output video 72 may have, as the predetermined image processing function, an image correction function such as a function of adjustment to a visually preferable color tone or a highlighting processing function for the inputted first image information signal (the image pickup signal relating to the endoscopic image outputted from the video processor 3).

<Configuration of the Information Analysis Circuit 53>

Subsequently, a configuration of the information analysis circuit 53 is explained in detail.

Figure 4:
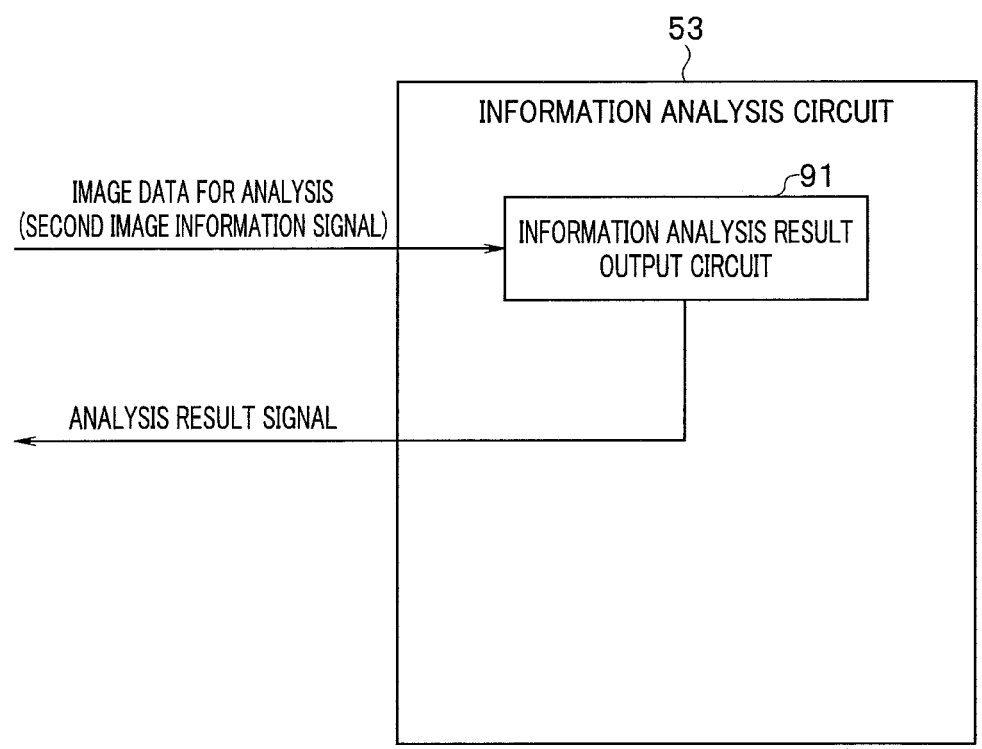
FIG. 4 is a block diagram showing a configuration of an information analysis circuit in the image processing apparatus in the first embodiment.

FIG. 4 is a block diagram showing the configuration of the information analysis circuit 53 in the image processing apparatus 5 in the present embodiment.

As explained above, in the present embodiment, the information analysis circuit 53 is configured by the GP-GPU 56. The information analysis circuit 53 receives the second image information signal (the image data for analysis) outputted from the video distribution circuit 51, applies a predetermined analysis (in the present embodiment, an analysis by recognition processing) to the second image information signal (the image data for analysis), and outputs an analysis result to the information addition circuit 52.

As shown in FIG. 4, the information analysis circuit 53 includes an information analysis result output circuit 91 that receives the second image information signal (the image data for analysis), carries out a predetermined analysis, and outputs an analysis result.

<Information Analysis Result Output Circuit 91>

The information analysis result output circuit 91 carries out, on the image data for analysis (the second image information signal) generated in the image processing circuit for information analysis 71 in the video distribution circuit 51, recognition processing relating to a so-called computer-aided diagnosis (CAD) function and image processing necessary for performing the recognition processing and outputs an analysis result relating to the recognition processing to the information addition circuit 52 at a post-stage.

As explained above, the computer-aided-diagnosis (CAD) is a system that performs, with an information processing technique by a computer or the like, quantization and an analysis of information concerning an image obtained by an endoscope or the like and actively uses a result of the quantization and the analysis for an image diagnosis to aid a doctor.

Figure 8:
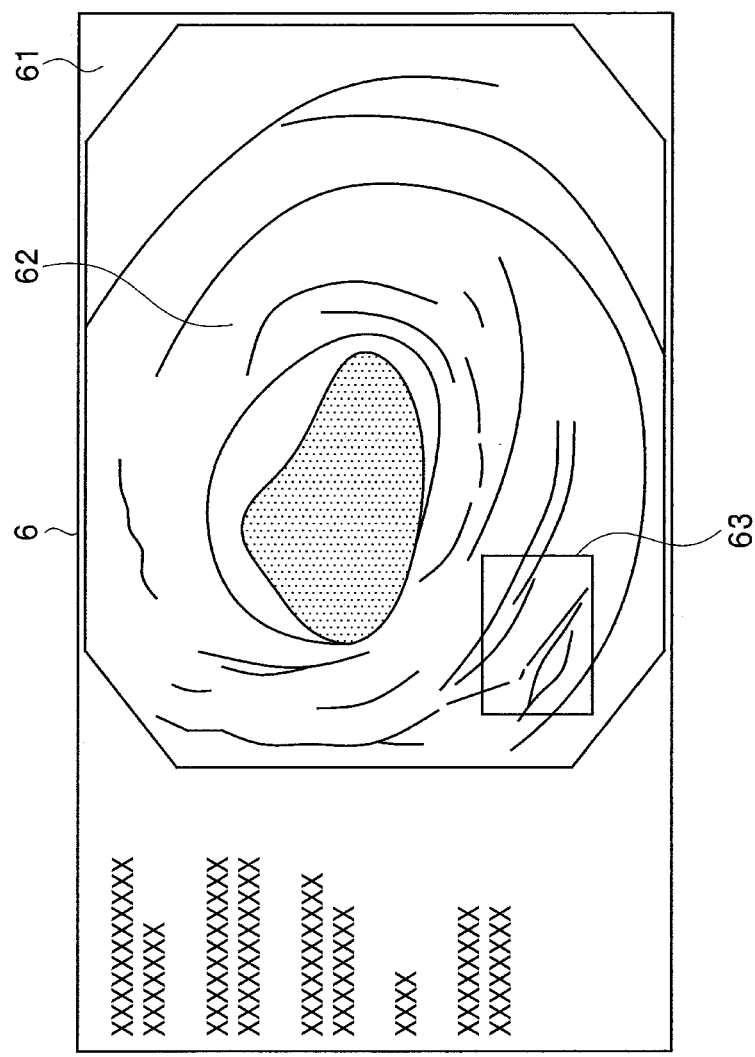
FIG. 8 is a diagram showing an example of an image region for recognition processing (for an information analysis) in the image processing apparatus in the first embodiment.

The information analysis result output circuit 91 plays a role of carrying out the recognition processing or the like relating to the computer-aided diagnosis (CAD) function, that is, plays a role of aiding decision making of a doctor by extracting, for example, a region of attention 63 shown in FIG. 8 from the image data for analysis (the second image information signal) generated in the image processing circuit for information analysis 71 and, for a case in which decision making such as malignity and benignancy discrimination of a quantitative result focus is difficult for the extracted region of attention, presenting information (quantitative numerical values analyzed by a computer) serving as material.

As explained above, the information analysis circuit 53 according to the present embodiment is configured by a GP-GPU (general-purpose computing on graphics processing units). As explained above, the GP-GPU is the general-purpose computation processing technique by the GPU (graphics processing units).

Incidentally, in the present embodiment, a GP-GPU, processing speed of which is further increased, is adopted. However, as explained above, the recognition processing used for the computer-aided diagnosis (CAD) function requires enormous computation processing. Accordingly, even if the GP-GPU increased in speed is adopted, in the information analysis circuit 53 in the present embodiment, it is likely that an analysis result signal to be outputted is delayed with respect to the inputted image data for analysis (second image information signal).

When such a delay occurs, since an image displayed on a monitor is delayed with respect to a movement of an endoscope, it is likely that endoscope operation is hindered. However, the present invention has been devised in view of such circumstances. Even if advanced recognition processing such as a computer-aided diagnosis (CAD) is carried out in the information analysis circuit 53 and accuracy of the recognition processing is further improved, the present invention makes it possible to suppress a delay effect of a video signal outputted from the image processing apparatus 5.

<Configuration of the Information Addition Circuit 52>

Subsequently, a configuration of the information addition circuit 52 is explained in detail.

Figure 5:
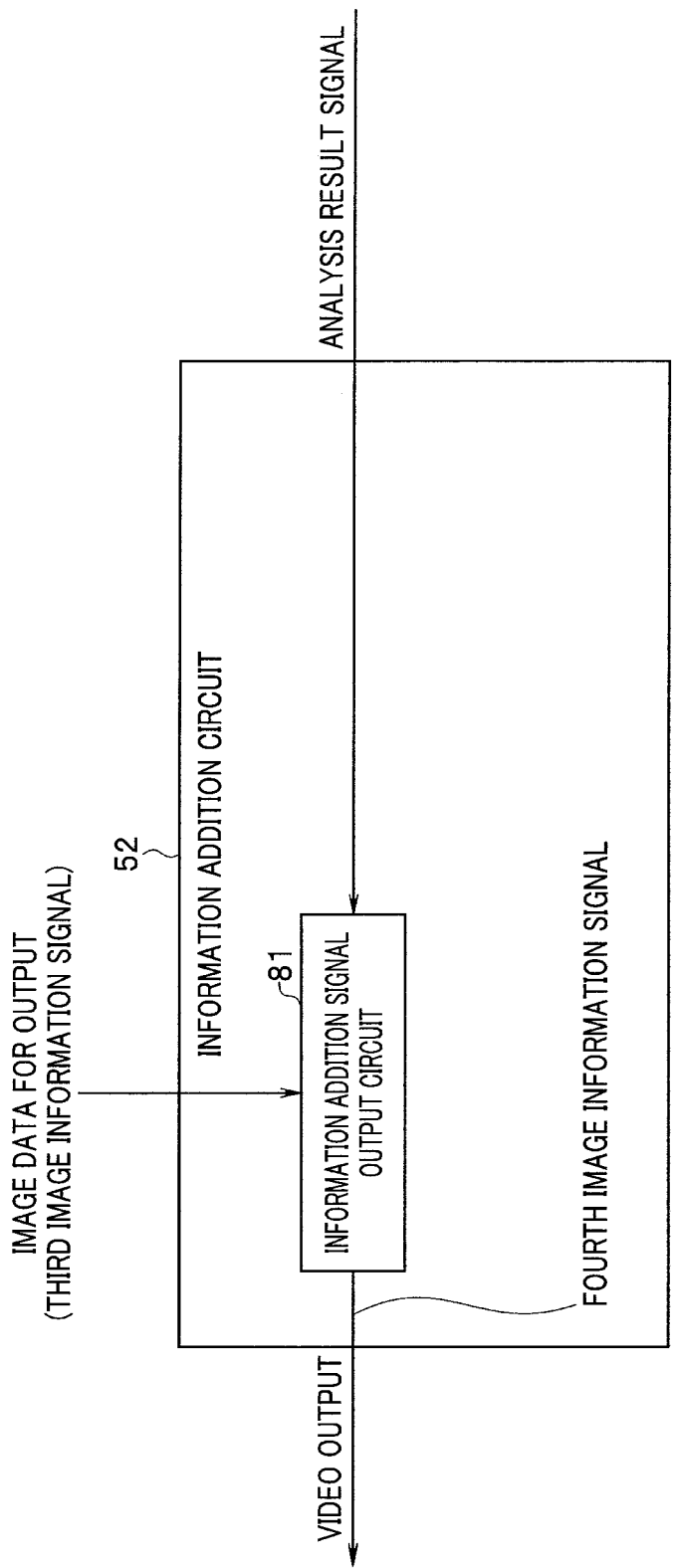
FIG. 5 is a block diagram showing a configuration of an information addition circuit in the image processing apparatus in the first embodiment.

FIG. 5 is a block diagram showing the configuration of the information addition circuit 52 in the image processing apparatus 5 in the present embodiment.

As explained above, in the present embodiment, the information addition circuit 52 is formed by the FPGA (field-programmable gate array) 55 together with the video distribution circuit 51. More specifically, an information addition signal output circuit 81 that receives the third image information signal and the analysis result signal is formed on the FPGA 55.

Note that the third image information signal is generated in the video distribution circuit 51 and outputted toward the information addition circuit 52. The analysis result signal is generated in the information analysis circuit 53 and outputted toward the information addition circuit 52.

<Information Addition Signal Output Circuit 81>

First, the information addition signal output circuit 81 receives the image data for output (the third image information signal) generated and outputted in the image processing circuit for output video 72 in the video distribution circuit 51. As explained above, the image data for output (the third image information signal) is obtained by applying, in the image processing circuit for output video 72, the predetermined image processing to the image pickup signal (the first image information signal) relating to the endoscopic image outputted from the video processor 3. The image data for output is outputted from the image processing circuit for output video 72 in a delay minimized state and inputted to the information addition signal output circuit 81.

On the other hand, the information addition signal output circuit 81 receives the analysis result signal outputted from the information analysis result output circuit 91 in the information analysis circuit 53.

The information addition signal output circuit 81 combines the image data for output (the third image information signal), the delay of which is minimized, and the analysis result signal in which a relatively large delay is likely to occur, generates the fourth image information signal, and outputs the fourth image information signal to, for example, the monitor 6 at a post-stage.

<Action in the Present Embodiment>

Subsequently, action in the present embodiment is explained with reference to FIG. 6.

Figure 6:
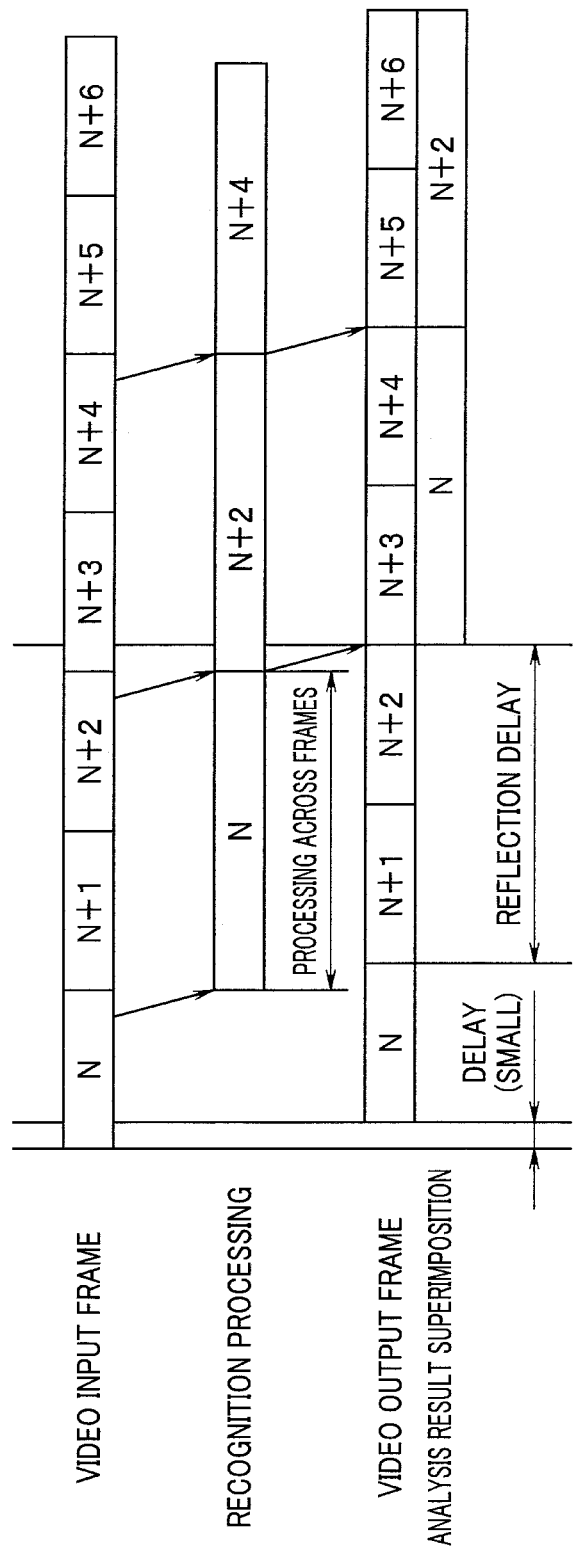
FIG. 6 is a timing chart for explaining action in the video distribution circuit, the information addition circuit, and the information analysis circuit in the image processing apparatus in the first embodiment.

FIG. 6 is a timing chart for explaining action in the video distribution circuit, the information addition circuit, and the information analysis circuit in the image processing apparatus in the first embodiment.

As explained above, the image data for analysis (the second image information signal) outputted from the image processing circuit for information analysis 71 in the video distribution circuit 51 is inputted to the information analysis result output circuit 91 in the information analysis circuit 53.

It is assumed that, now, as shown in FIG. 6, video input frames relating to the first image information signal inputted to the video distribution circuit 51 are (N, N+1, N+2, N+3, N+4, N+5, N+6, . . . ). In the image processing circuit for information analysis 71 in the video distribution circuit 51, as explained above, the image data for analysis is generated based on this video input and outputted toward the information analysis circuit 53 as the second image information signal.

Note that the third image information signal, a delay of which is minimized with respect to the first image information signal, is outputted from the video distribution circuit 51 to the information addition circuit 52 as the image data for output.

Thereafter, the recognition processing explained above is applied to the second image information signal in the information analysis result output circuit 91 in the information analysis circuit 53 to which the second image information signal is inputted. At this time, for example, as shown in FIG. 6, the information analysis result output circuit 91 performs the recognition processing relating to the frame N across continuous frames of the frame N and the frame N+1. The information analysis result output circuit 91 outputs an analysis result signal relating to the recognition processing to the information addition circuit 52 at a post-stage.

Further, the information analysis result output circuit 91 performs the recognition processing relating to the frame N+2 across continuous frames of the frame N+2 and the frame N+3 and outputs an analysis result signal relating to the recognition processing to the information addition circuit 52 at the post-stage following the analysis result signal relating to the frame N explained above.

First, the information addition signal output circuit 81 in the information addition circuit 52 receives the image data for output (the third image information signal) generated and outputted in the image processing circuit for output video 72 in the video distribution circuit 51. As explained above, the image data for output (the third image information signal) is outputted in the delay minimized state. In the information addition signal output circuit 81, this signal is outputted as a video output frame shown in FIG. 6.

On the other hand, the information addition signal output circuit 81 superimposes analysis results continuously outputted in time series as explained above from the information analysis result output circuit 91 in the information analysis circuit 53 on the video output frame. More specifically, the information addition signal output circuit 81 performs processing for superimposing, as appropriate, the analysis results obtained as explained above in the information analysis result output circuit 91, that is, the analysis result of the recognition processing relating to the frame N, the analysis result of the recognition processing relating to the frame N+2, and the like on the video output frames (N, N+1, N+2, N+3, N+4, N+5, N+6, . . . ).

The information addition signal output circuit 81 in the information addition circuit 52 outputs the video output frames (N, N+1, N+2, N+3, N+4, N+5, N+6, . . . ) superimposed with the analysis results to, for example, the monitor 6 at a post-stage as the fourth image information signal.

As explained above, the image data for output (the third image information signal) outputted from the video distribution circuit 51 (the image processing circuit for output video 72) toward the information addition circuit 52 (the information addition signal output circuit 81) is outputted in the delay minimized state. This signal is outputted from the information addition signal output circuit 81 as a video output frame. More specifically, as shown in FIG. 6, for example, when a period of one frame is represented as "f", a delay of the video output frame with respect to the video input frame is "0.1 f" or less.

In contrast, when an analysis result obtained through the first route (that is, an information analysis processing route for applying, in the information analysis circuit 53, the predetermined recognition processing to the second image information signal outputted from the video distribution circuit 51 and outputting an analysis result in the recognition processing toward the information addition circuit 52) is superimposed on the video output frame, it is likely that a delay for several frames occurs in a frame on which the analysis result is actually reflected.

More specifically, for example, as shown in FIG. 6, it is also conceivable that the analysis result of the recognition processing relating to the frame N is superimposed on the frames N+3 to N+4 in the video output frame and the analysis result of the recognition processing relating to the frame N+2 is superimposed on the frames N+5 to N+6 in the video output frame. In this case, a reflection delay for several frames occurs.

In this way, a video signal, to which recognition processing is actually applied, in the "analysis result signal" outputted from the information analysis circuit 53 (the information analysis result output circuit 91) is in a state in which the video signal is delayed for several frames (in the example shown in FIG. 6, for approximately three frames) with respect to the image data for analysis (the second image information signal) at time point when the video signal is inputted to the information analysis circuit 53.

However, in the image processing apparatus 5 in the present embodiment, although, in the analysis result signal through the first route (the analysis result signal applied with the recognition processing in the information analysis circuit 53), a delay for several frames certainly occurs with respect to the video input frame, the fourth image information signal actually outputted from the information addition circuit 52 outputs the video output frame based on the image information signal (the third image information signal) from the second route, the delay of which is minimized Therefore, an unnatural feeling due to the delay of the image signal displayed on the monitor does not occur.

On the other hand, since the analysis result delayed for several frames but applied with the recognition processing is superimposed on the video output frame, the delay of which is minimized, it is possible to add necessary and sufficient recognition processing analysis information to the image signal displayed on the monitor.

As explained above, the image processing apparatus 5 in the present invention makes it possible to provide the route (the second route) for receiving the first image information signal (for example, the image including the endoscopic image) continuously outputted from the external apparatus (in the present embodiment, the video processor 3) and outputting the image signal (the third image information signal), the delay of which is minimized with respect to the inputted first image information signal and the route (the first route) for generating and outputting the second image information signal applied with a preprocess for applying the predetermined analysis (for example, the information analysis such as the recognition processing) to the first image information signal and generating and outputting the analysis result signal obtained by applying the information analysis such as the recognition processing to the second image information signal and combine the third image information signal, the delay of which is minimized, and the analysis result signal accurately applied with the information analysis such as the recognition processing and output a combined signal as the fourth image information signal.

Consequently, with the image processing apparatus in the present embodiment, it is possible to provide an image processing apparatus that, even if recognition processing that has a heavy processing load and easily causes a relatively large delay is carried out, can suppress a delay effect of an outputted video signal.

The image processing apparatus in the present embodiment can easily apply correction or highlighting correction to a visually preferable color tone to the third image information signal, the delay of which relating to the second route is minimized. The image processing apparatus makes it possible to carry out advanced recognition processing such as a computer-aided diagnosis (CAD) with a less influence of a delay while maintaining quality of an image provided to a user.

Second Embodiment

Subsequently, a second embodiment of the present invention is explained.

Main components of an image processing apparatus in the second embodiment are the same as the components in the first embodiment but only a configuration of an information analysis circuit is different. Therefore, only the difference from the first embodiment is explained and explanation about common portions is omitted.

<Configuration of an Information Analysis Circuit 253 in the Second Embodiment>

Figure 9:
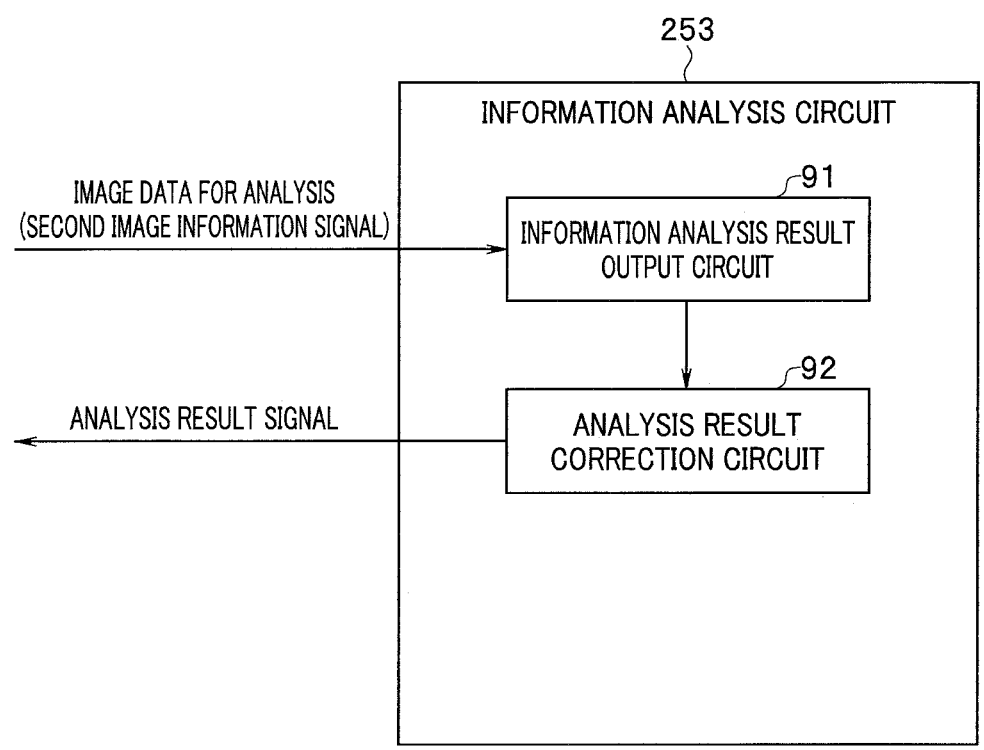
FIG. 9 is a block diagram showing a configuration of an information analysis circuit in an image processing apparatus in a second embodiment of the present invention.

FIG. 9 is a block diagram showing a configuration of an information analysis circuit in the image processing apparatus in the second embodiment of the present invention.

In the second embodiment, the information analysis circuit 253 is configured by a GP-GPU as in the first embodiment and includes the information analysis result output circuit 91 that receives a second image information signal (image data for analysis) outputted from the video distribution circuit 51, applies a predetermined analysis (in the present embodiment, an analysis by recognition processing) to the second image information signal (the image data for analysis), and outputs an analysis result.

As shown in FIG. 9, the information analysis circuit 253 includes an analysis result correction circuit 92 that applies predetermined correction to the analysis result outputted from the information analysis result output circuit 91 and, thereafter, outputs a signal of the corrected analysis result toward the information addition circuit 52 at a post-stage.

As in the first embodiment, in the second embodiment, the information analysis result output circuit 91 carries out, on the image data for analysis (the second image information signal) generated in the image processing circuit for information analysis 71 in the video distribution circuit 51, recognition processing relating to a so-called computer-aided diagnosis (CAD) function and image processing necessary for performing the recognition processing and outputs an analysis result relating to the recognition processing to the analysis result correction circuit 92 at a post-stage.

The analysis result correction circuit 92 corrects the analysis result based on at least continuous two analysis results among analysis results relating to the recognition processing outputted from the information analysis result output circuit 91 continuously in time series and outputs the corrected analysis result toward the information addition signal output circuit 81 in the information addition circuit 52 as an analysis result signal. More specifically, the analysis result correction circuit 92 analyzes a movement in an image of a region of attention in a continuous image based on the at least continuous two analysis results and outputs, as the analysis result signal, a result obtained by optimizing a position of a frame to be superimposed.

With the action of the analysis result correction circuit 92, even if a delay occurs in superimposition of the analysis results, it is possible to correct the analysis results with a movement amount and, for example, when an analysis result of an N+2 frame is superimposed on N+5, estimate, from an analysis result of an N frame and an analysis result of the N+2 frame, where the region of attention seems to be located in the N+5 frame.

In the second embodiment, the information addition circuit 52 superimposes the corrected analysis result signal outputted from the analysis result correction circuit 92 on a third image information signal (see the video output frame shown in FIG. 6).

The other components and action are the same as those in the components and the action in the first embodiment.

In the image processing apparatus in the second embodiment, the same effects as the effects in the first embodiment are achieved. The analysis result is corrected based on the at least continuous two analysis results. Consequently, it is possible to superimpose more accurate recognition processing analysis information on the video output frame.

Third Embodiment

Subsequently, a third embodiment of the present invention is explained.

Figure 10:
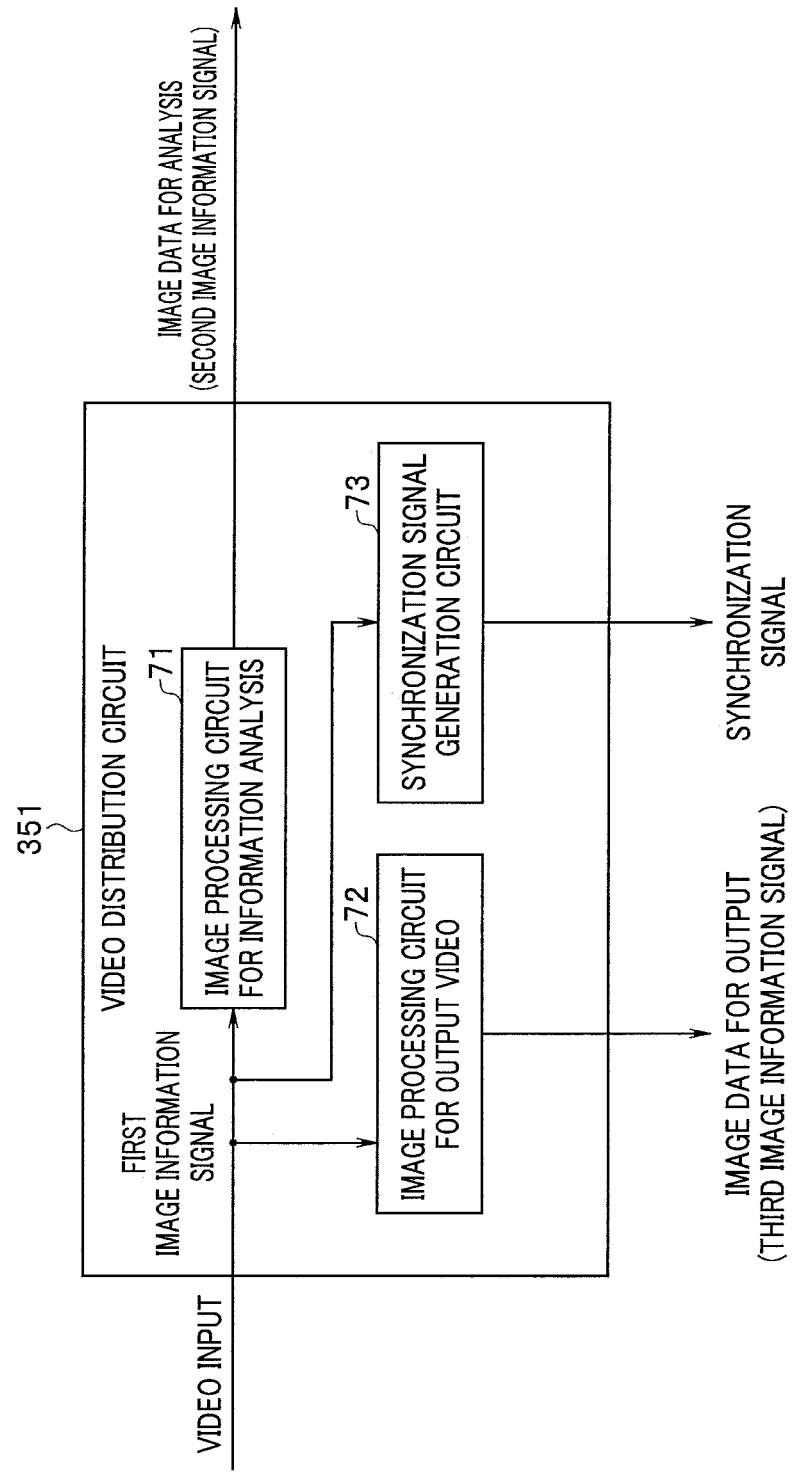
FIG. 10 is a block diagram showing a configuration of a video distribution circuit in an image processing apparatus in a third embodiment of the present invention.
Figure 11:
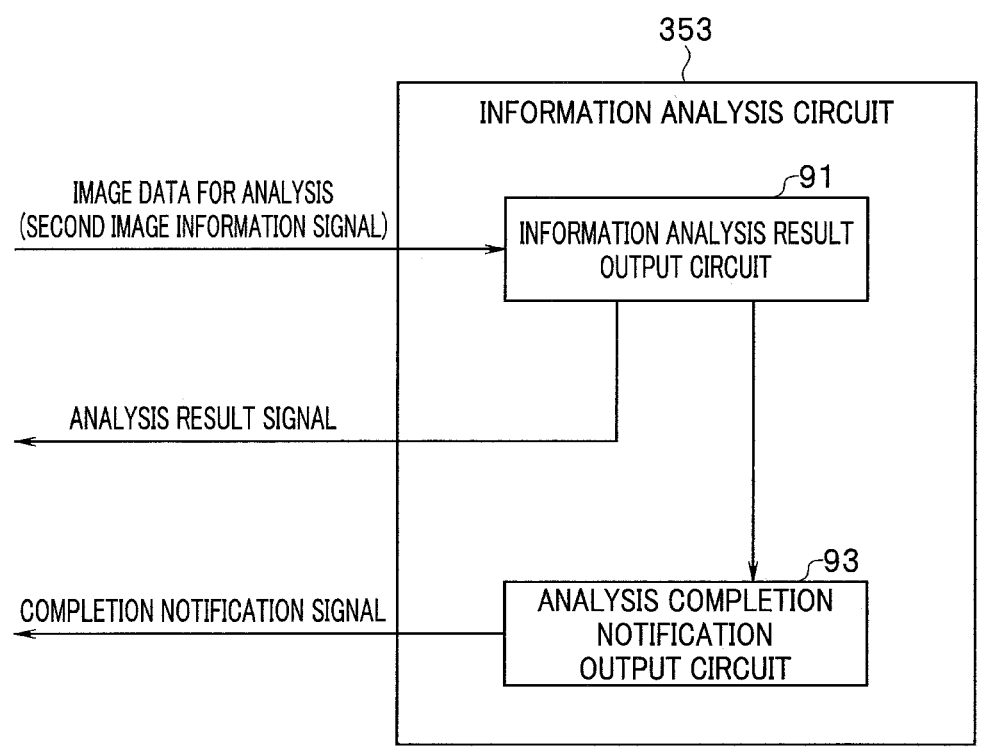
FIG. 11 is a block diagram showing a configuration of an information analysis circuit in the image processing apparatus in the third embodiment.
Figure 12:
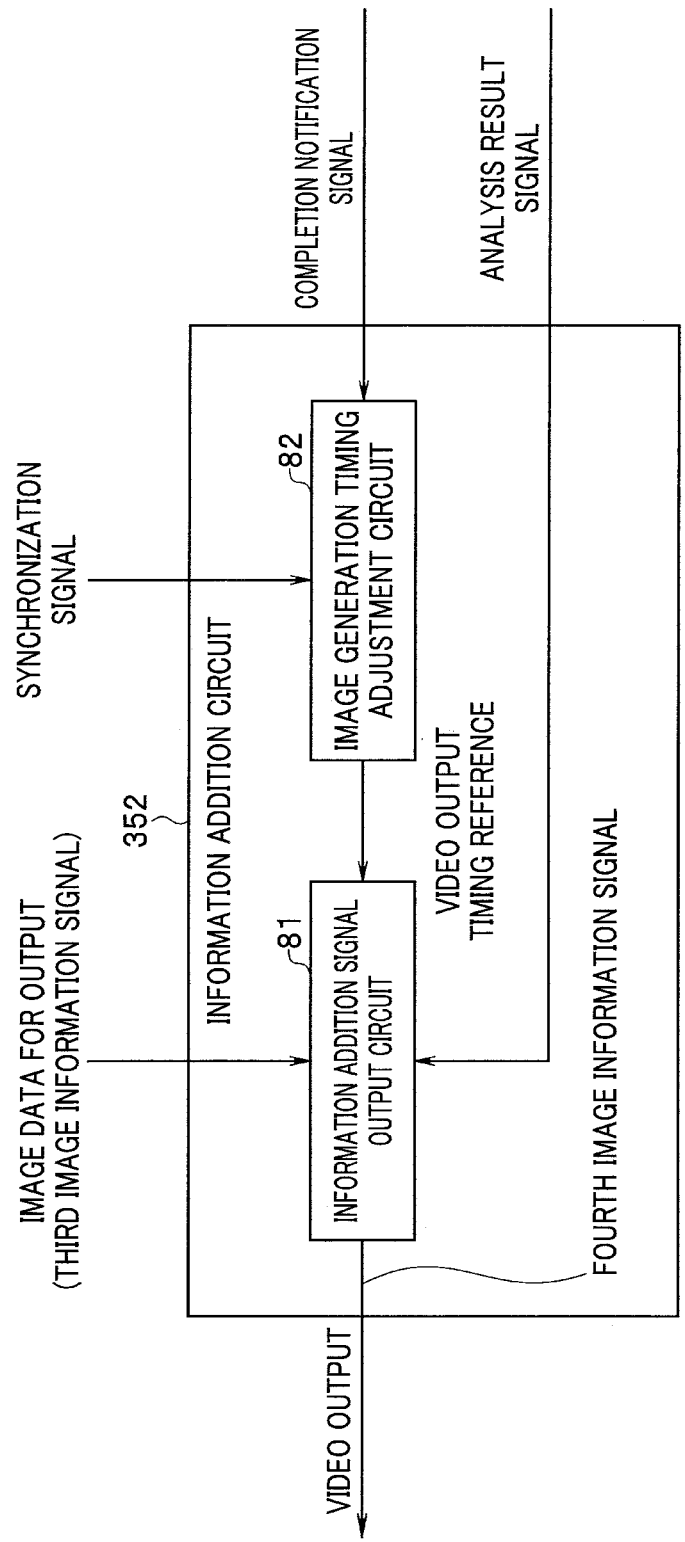
FIG. 12 is a block diagram showing a configuration of an information addition circuit in the image processing apparatus in the third embodiment.

FIG. 10 is a block diagram showing a configuration of a video distribution circuit in an image processing apparatus in the third embodiment of the present invention. FIG. 11 is a block diagram showing a configuration of an information analysis circuit in the image processing apparatus in the third embodiment. FIG. 12 is a block diagram showing a configuration of an information addition circuit in the image processing apparatus in the third embodiment.

Main components of the image processing apparatus in the third embodiment are the same as the components in the first embodiment but configurations of a video distribution circuit 351, an information analysis circuit 353, and an information addition circuit 352 are different. Only the difference from the first embodiment is explained and explanation about common portions is omitted.

In the third embodiment as well, the video distribution circuit 351 and the information addition circuit 352 are configured as circuits formed in a so-called FPGA (field-programmable gate array) 55 disposed in the image processing apparatus 5.

In the third embodiment, the information analysis circuit 353 is a circuit configured by a GP-GPU (general-purpose computing on graphics processing units), which is a general-purpose computation processing technique by a GPU (graphics processing units).

<Configuration of the Video Distribution Circuit 351 in the Third Embodiment>

FIG. 10 is a block diagram showing a configuration of the video distribution circuit 351 in the third embodiment.

In the third embodiment as well, the video distribution circuit 351 receives a first image information signal continuously outputted from the video processor 3, which is an external apparatus, outputs a second image information signal corresponding to the inputted first image information signal to at least a first route, and outputs a third image information signal, which is an image information signal corresponding to the first image information signal and is different from the second image information signal, to a second route.

As in the first embodiment, the video distribution circuit 351 in the third embodiment includes the image processing circuit for information analysis 71 that generates the second image information signal (image data for analysis) based on the first image information signal and outputs the second image information signal. Action, effects and the like of the image processing circuit for information analysis 71 are the same as the action, effects and the like in the first embodiment. Therefore, explanation about the action, effects and the like of the image processing circuit for information analysis 71 is omitted.

On the other hand, the video distribution circuit 351 includes the image processing circuit for output video 72 that generates the third image information signal based on the first image information signal and outputs the third image information signal. Action, effects and the like of the image processing circuit for output video 72 are the same as the action, effects and the like in the first embodiment. Therefore, explanation about the action, effects and the like of the image processing circuit for output video 72 is omitted.

<Synchronization Signal Generation Circuit 73>

The video distribution circuit 351 in the third embodiment includes a synchronization signal generation circuit 73 that generates and outputs a synchronization signal synchronized with the first image information signal. The synchronization signal generated in the synchronization signal generation circuit 73 is outputted to an image generation timing adjustment circuit 82 in the information addition circuit 352 explained below.

Note that, in the third embodiment, the synchronization signal generation circuit 73 is provided in the video distribution circuit 351. However, the synchronization signal generation circuit 73 is not limited thereto and may be formed in another part in the FPGA 55. The synchronization signal generation circuit 73 may be configured as a circuit other than the FPGA 55.

<Configuration of the Information Analysis Circuit 353 in the Third Embodiment>

Subsequently, a configuration of the information analysis circuit 353 in the third embodiment is explained in detail.

FIG. 11 is a block diagram showing a configuration of the information analysis circuit 353 in the third embodiment.

In the third embodiment, as explained above, the information analysis circuit 353 is configured by the GP-GPU as in the first embodiment. The information analysis circuit 353 receives the second image information signal (the image data for analysis) outputted from the video distribution circuit 351, applies a predetermined analysis (in the present embodiment, an analysis by recognition processing) to the second image information signal (the image data for analysis), and outputs an analysis result toward the information addition circuit 352.

As shown in FIG. 11, the information analysis circuit 353 includes the information analysis result output circuit 91 that receives the second image information signal (the image data for analysis), carries out a predetermined analysis, and outputs an analysis result and an analysis completion notification output circuit 93 that generates a predetermined completion notification signal every time the analysis in the information analysis result output circuit 91 is completed and outputs the predetermined completion notification signal toward the information addition circuit 52.

Note that main action and effects of the information analysis result output circuit 91 in the third embodiment are the same as the main action and effects in the first embodiment. Therefore, explanation about the main action and effects is omitted.

<Analysis Completion Notification Output Circuit 93>

The analysis completion notification output circuit 93 in the third embodiment generates, every time the analysis result of the recognition processing relating to the second image information signal, that is, an "analysis result signal" is outputted from the information analysis result output circuit 91, a "completion notification signal" indicating that the analysis is completed and outputs the "completion notification signal" toward the image generation timing adjustment circuit 82 in the information addition circuit 352.

<Configuration of the Information Addition Circuit 352 in the Third Embodiment>

Subsequently, a configuration of the information addition circuit 352 in the third embodiment is explained in detail.

FIG. 12 is a block diagram showing a configuration of the information addition circuit 352 in the present embodiment.

In the third embodiment, as in the first embodiment, the information addition circuit 352 is formed by an FPGA (field-programmable gate array) together with the video distribution circuit 351. More specifically, the information addition signal output circuit 81 that receives the third image information signal and the analysis result signal and the image generation timing adjustment circuit 82 that receives the synchronization signal and the completion notification signal are formed on the FPGA 55.

Note that both of the third image information signal and the synchronization signal are generated in the video distribution circuit 351 and outputted toward the information addition circuit 352. Both of the analysis result signal and the completion notification signal are generated in the information analysis circuit 353 and outputted toward the information addition circuit 352.

<Image Generation Timing Adjustment Circuit 82>

In the third embodiment, first, the image generation timing adjustment circuit 82 receives the synchronization signal generated in the synchronization signal generation circuit 73 in the video distribution circuit 351. The synchronization signal is a synchronization signal generated in the synchronization signal generation circuit 73 based on the first image information signal inputted to the video distribution circuit 351 as explained above.

On the other hand, the image generation timing adjustment circuit 82 receives the "completion notification signal" outputted from the analysis completion notification output circuit 93 in the information analysis circuit 353. As explained above, the "completion notification signal" is a signal that, every time the analysis result of the recognition processing relating to the second image information signal, that is, the "analysis result signal" is outputted, indicates that the analysis is completed.

Immediately after the information addition signal output circuit 81 receives the analysis result signal, the image generation timing adjustment circuit 82 generates a video output timing reference signal based on the synchronization signal such that the analysis result can be superimposed on an appropriate frame of a video output frame and outputs the video output timing reference signal toward the information addition signal output circuit 81.

Note that the image generation timing adjustment circuit 82 generates, as the video output timing reference signal, a signal having a predetermined phase difference with respect to the synchronization signal outputted from the synchronization signal generation circuit 73. Alternatively, the image generation timing adjustment circuit 82 generates, as the video output timing reference signal, a signal having a predetermined temporal difference with respect to the synchronization signal outputted from the synchronization signal generation circuit 73. Further, the image generation timing adjustment circuit 82 generates, as the video output timing reference signal, a signal obtained by multiplying or dividing the synchronization signal outputted from the synchronization signal generation circuit 73.

<Information Addition Signal Output Circuit 81 in the Third Embodiment>

On the other hand, in the third embodiment, as in the first embodiment, first, the information addition signal output circuit 81 receives the image data for output (the third image information signal) generated and outputted in the image processing circuit for output video 72 in the video distribution circuit 351.

On the other hand, the information addition signal output circuit 81 receives the analysis result signal outputted from the information analysis result output circuit 91 in the information analysis circuit 353 and further receives the video output timing reference signal outputted from the image generation timing adjustment circuit 82.

In the third embodiment, according to timing of the video output timing reference signal, immediately after receiving the analysis result signal from the information analysis circuit 353, the information addition signal output circuit 81 superimposes the analysis result on the appropriate frame of the video output frame.

Figure 13:
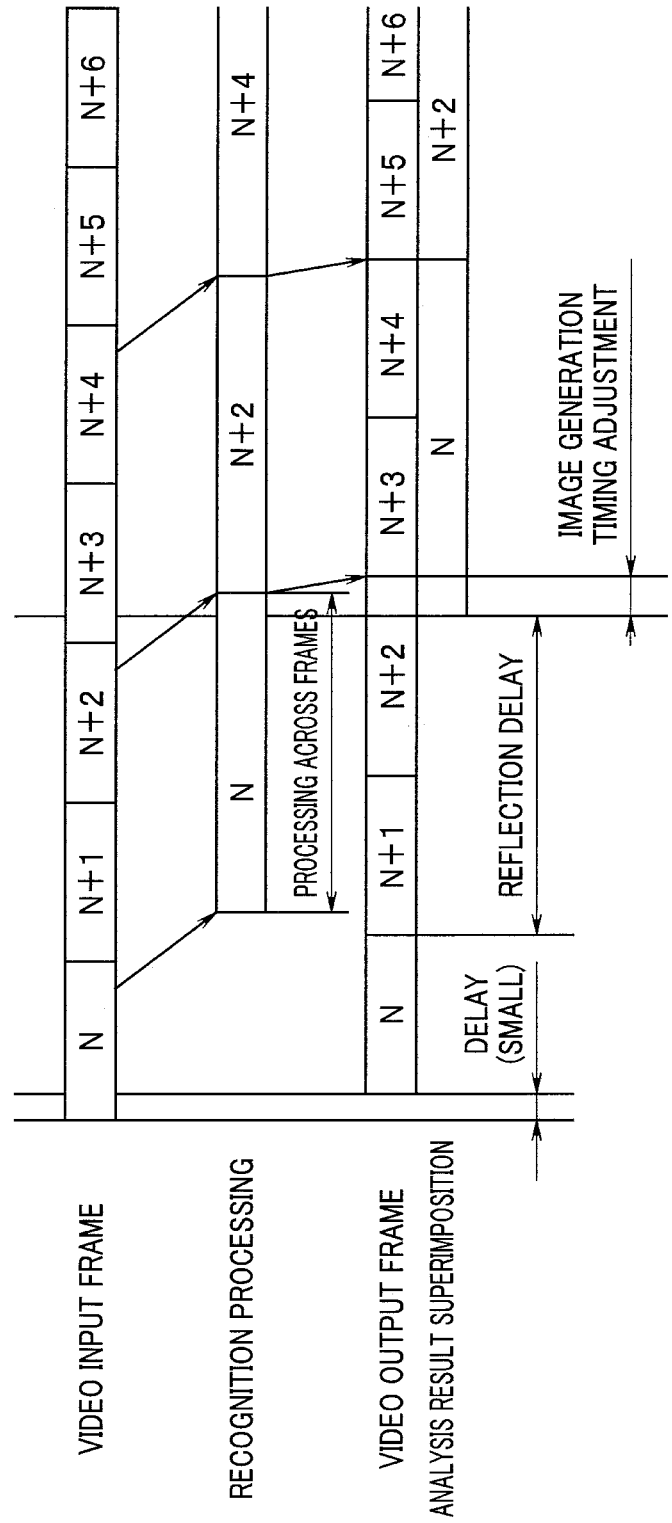
FIG. 13 is a timing chart for explaining action in the video distribution circuit, the information addition circuit, and the information analysis circuit in the image processing apparatus in the third embodiment.

FIG. 13 is a timing chart for explaining action in the video distribution circuit, the information addition circuit, and the information analysis circuit in the image processing apparatus in the third embodiment.

More specifically, for example, as shown in FIG. 13, when processing across frames is applied in the recognition processing in the information analysis circuit 353 now, when a "completion notification signal" relating to a frame "N" received by the information addition signal output circuit 81 is at timing slightly after start timing of a frame "N+3" in the video output frame, the image processing apparatus 5 performs control to slightly shift the start timing of the frame "N+3" according to the video output timing reference signal outputted from the image generation timing adjustment circuit 82 and superimpose an analysis result signal relating to the frame "N" on the frame "N+3".

In this way, with the image processing apparatus in the third embodiment, by controlling timing for superimposing the analysis result signal on the video output frame, immediately after receiving the analysis result signal in the information analysis circuit 353, it is possible to superimpose the analysis result signal on an appropriate frame of the video output frame and more accurately reflect a recognition processing result on an output image signal.

The present invention is not limited to the embodiments explained above. Various changes, alterations, and the like are possible in a range in which the gist of the present invention is not changed.

What is claimed is:

1. An image processing apparatus comprising:
a processor comprising hardware, wherein the processor is configured to:
continuously receive first image information signals, where each of the first image information signals corresponds to one of a plurality of input frames;
output a second image information signal, based on one of the first image information signals corresponding to a first input frame of the plurality of input frames, to at least a first route;
continuously output third image information signals, where each of the third image information signals is based on a corresponding one of the first image information signals, to a second route;
apply a predetermined analysis to the second image information signal and output a result of the predetermined analysis; and
generate and continuously output fourth image information signals, where each of the fourth image information signals corresponds to one of a plurality of output frames,
wherein each of the fourth image information signals is based on a corresponding one of the first image information signals,
wherein, where a period of each of the plurality of input frames is f, output of the each of the fourth image information signals is delayed relative to the receipt of the corresponding one of the first image information signals by xf, where x is less than 1,
wherein one of the fourth image information signals is based on one of the third image information signals based on the one of the first image information signals corresponding to the first input frame, and
wherein a subsequent one of the fourth image information signals outputted is based on a subsequent one of the third image information signals with information based on the result of the predetermined analysis superimposed thereon, with superimposition of the information based on the result of the predetermined analysis being started in the generation of the subsequent one of the fourth image information signals and the generation of the subsequent one of the fourth image information signals is delayed relative to the receipt of the one of the first image information signals by yf, where y is greater than 1.

2. The image processing apparatus according to claim 1, wherein the processor is configured to:
generate image data for analysis based on the first image information signal corresponding to the first input frame; and
output the image data for analysis to the first route as the second image information signal.

3. The image processing apparatus according to claim 2, wherein the processor is configured to:
segment a predetermined region in the first image information signal corresponding to the first input frame;
generate the image data for analysis relating to the predetermined region; and
output the image data for analysis to the first route as the second image information signal.

4. The image processing apparatus according to claim 2, wherein the processor is configured to:
generate the image data for analysis by leveling a predetermined physical characteristic relating to the first image information signal; and
output the image data for analysis to the first route as the second image information signal.

5. The image processing apparatus according to claim 1, wherein the processor is configured to:
generate the third image information signals by applying predetermined image processing to the first image information signals; and
output the third image information signals to the second route.

6. The image processing apparatus according to claim 1, wherein the processor is configured to:
generate a synchronization signal synchronized with the first image information signal corresponding to the first input frame; and
generate the subsequent one of the fourth image information signal according to a timing reference based on the synchronization signal.

7. The image processing apparatus according to claim 6, wherein the processor is configured to generate the subsequent one of the fourth image information signal using, as the timing reference, a signal having a predetermined phase difference with respect to the synchronization signal.

8. The image processing apparatus according to claim 7, wherein the processor is configured to:
generate, every time the processor outputs the result of the predetermined analysis relating to the second image information signal, an analysis completion notification signal indicating that the predetermined analysis is completed; and
generate the subsequent one of fourth image information signal using, as the timing reference, a temporal difference from the synchronization signal every time the processor generates the analysis completion notification signal.

9. The image processing apparatus according to claim 6, wherein the processor is configured to generate the subsequent one of fourth image information signal using, as the timing reference, a signal obtained by multiplying or dividing the synchronization signal.

10. The image processing apparatus according to claim 1, wherein the processor is configured to correct the result of the predetermined analysis based on at least two other results of the predetermined analysis continuous in time series.

11. An endoscope system comprising:
an endoscope configured to observe a subject and continuously output first image information signals, where each of the first image information signals corresponds to one of the plurality of input frames; and
the image processing apparatus according to claim 1.

12. The image processing apparatus according to claim 1, wherein a delay of the one of third image information signals based on the corresponding one of the first image information signal corresponding to the first input frame is equal to or less than one tenth of a period of the first input frame.

13. An image processing method comprising:
continuously receiving first image information signals, where each of the first image information signals corresponds to one of a plurality of input frames;
outputting a second image information signal, based on one of the first image information signals corresponding to a first input frame of the plurality of input frames, to at least a first route;
continuously outputting third image information signals, where each of the third image information signals is based on a corresponding one of the first image information signals, to a second route;
applying a predetermined analysis to the second image information signal and outputting a result of the predetermined analysis; and
generating and continuously outputting fourth image information signals, where each of the fourth image information signals corresponds to one of a plurality of output frames,
wherein each of the fourth image information signals is based on a corresponding one of the first image information signals,
wherein, where a period of each of the plurality of input frames is f, output of the each of the fourth image information signals is delayed relative to the receipt of the corresponding one of the first image information signals by xf, where x is less than 1,
wherein one of the fourth image information signals is based on one of the third image information signals based on the one of the first image information signals corresponding to the first input frame, and
wherein a subsequent one of the fourth image information signals outputted is based on a subsequent one of the third image information signals with information based on the result of the predetermined analysis superimposed thereon, with superimposition of the information based on the result of the predetermined analysis being started in the generation of the subsequent one of the fourth image information signals and the generation of the subsequent one of the fourth image information signals is delayed relative to the receipt of the one of the first image information signals by yf, where y is greater than 1.

14. An image processing method comprising:
outputting a second image information signal based on a first image information signal to at least a first route;
outputting a third image information signal based on the first image information signal to a second route;
receiving an analysis result based on an application of a predetermined analysis to the second image information signal;
generating a fourth image information signal based on the third image information signal; and
starting superimposing an information generated based on the analysis result on the fourth image information signal with delay for at least equal to or more than one period of one frame of the first image information signal after starting the generation of the fourth image information signal.

15. The image processing method according to claim 14, wherein
generating a synchronization signal synchronized with the first image information signal; and
generating the fourth image information signal according to a timing reference based on the synchronization signal.

16. The image processing method according to claim 15, wherein generating the fourth image information signal using, as the timing reference, a signal having a predetermined phase difference with respect to the synchronization signal.

17. The image processing method according to claim 16, wherein
generating, every time outputting the analysis result relating to the second image information signal, an analysis completion notification signal indicating that the analysis is completed; and
generating the fourth image information signal using, as the timing reference, a temporal difference from the synchronization signal every time generating the analysis completion notification signal.

18. The image processing method according to claim 15, wherein generating the fourth image information signal using, as the timing reference, a signal obtained by multiplying or dividing the synchronization signal.

* * * * *